(12) United States Patent
Adelberg

(10) Patent No.: US 8,313,081 B2
(45) Date of Patent: Nov. 20, 2012

(54) PARALLEL-ACTING ROLLER CLAMP FOR INTRAVENOUS ADMINISTRATION SET

(76) Inventor: Kenneth N. Adelberg, Encino, CA (US)

(*) Notice: Subject to any disclaimer, the term of this patent is extended or adjusted under 35 U.S.C. 154(b) by 1047 days.

(21) Appl. No.: 11/548,215

(22) Filed: Oct. 10, 2006

(65) Prior Publication Data

US 2008/0083890 A1  Apr. 10, 2008

(51) Int. Cl.
*F16K 7/04* (2006.01)
(52) U.S. Cl. .................. 251/6; 604/34
(58) Field of Classification Search ............ 251/6, 4; 604/34

See application file for complete search history.

(56) References Cited

U.S. PATENT DOCUMENTS

| | | | |
|---|---|---|---|
| 2,595,511 A | 5/1952 | Butler | |
| 3,685,787 A | 8/1972 | Adelberg | |
| 3,893,468 A | 7/1975 | McPhee | |
| 3,918,675 A | 11/1975 | Forberg | |
| 4,013,263 A | 3/1977 | Adelberg | |
| 4,047,694 A * | 9/1977 | Adelberg | 251/6 |
| 4,065,093 A * | 12/1977 | Phillips | 251/6 |
| 4,270,725 A | 6/1981 | Scott et al. | |
| 4,335,866 A * | 6/1982 | Bujan | 251/9 |
| RE31,584 E | 5/1984 | Adelberg | |
| 4,662,599 A | 5/1987 | Attermeier | |
| 4,869,721 A * | 9/1989 | Karpisek | 604/250 |
| 4,974,811 A * | 12/1990 | Ishida | 251/6 |
| 5,014,962 A | 5/1991 | Adelberg | |
| 6,129,330 A * | 10/2000 | Guala | 251/6 |
| 6,422,529 B1 | 7/2002 | Adelberg | |

* cited by examiner

*Primary Examiner* — John Bastianelli
*Assistant Examiner* — Andrew J Rost
(74) *Attorney, Agent, or Firm* — Sheppard, Mullin, Richter & Hampton, LLP

(57) ABSTRACT

An improved parallel-acting roller clamp is disclosed, for regulating fluid flow through a deformable plastic tube with improved control of fluid flow rate. The roller clamp achieves this improved performance by configuring a tapered relief groove formed in the clamp's bottom wall to have a reduced taper angle in the clamp's low-flow region. This minimizes variations in flow rate over time, due to cold flow, or creep, of the pinched, deformable plastic tube.

12 Claims, 4 Drawing Sheets

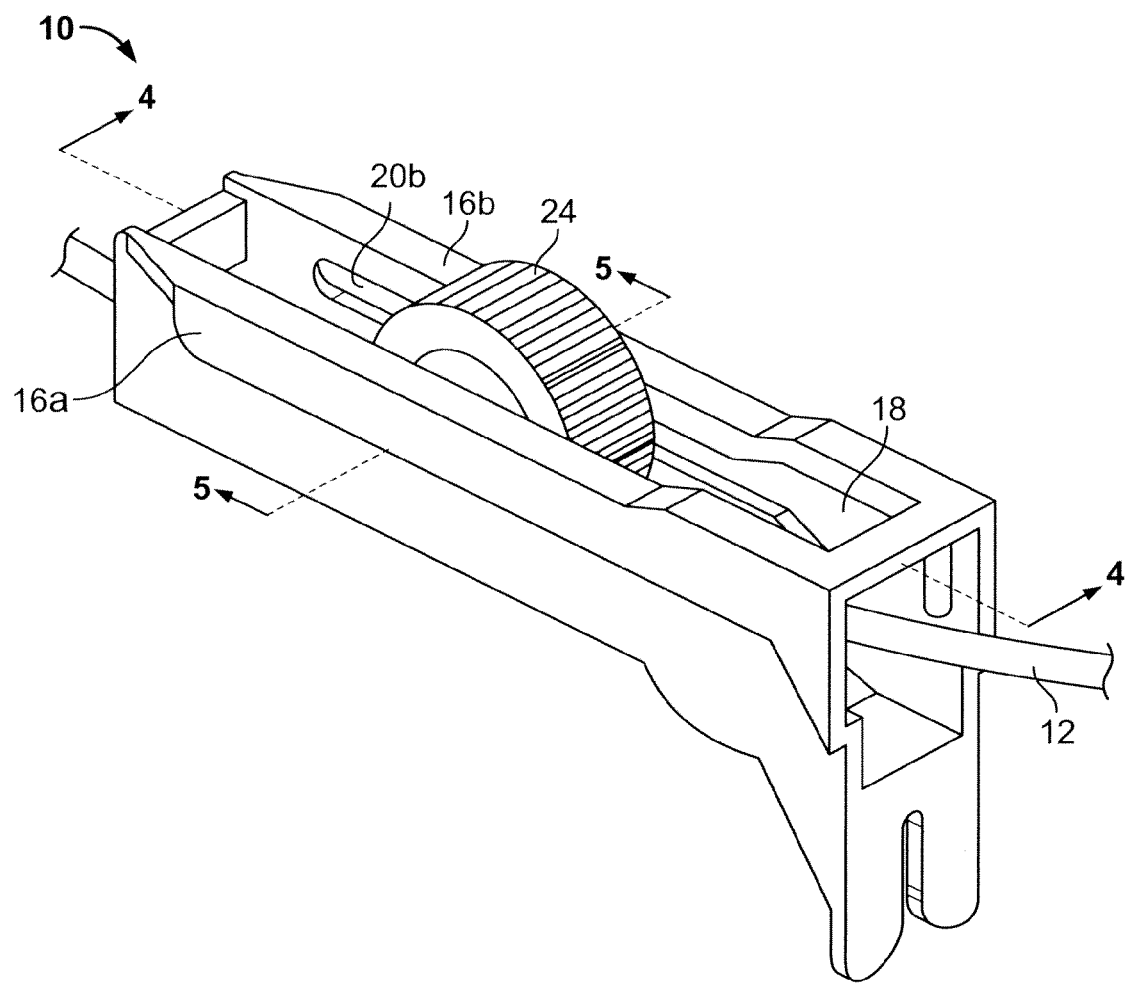
Amended FIG. 1

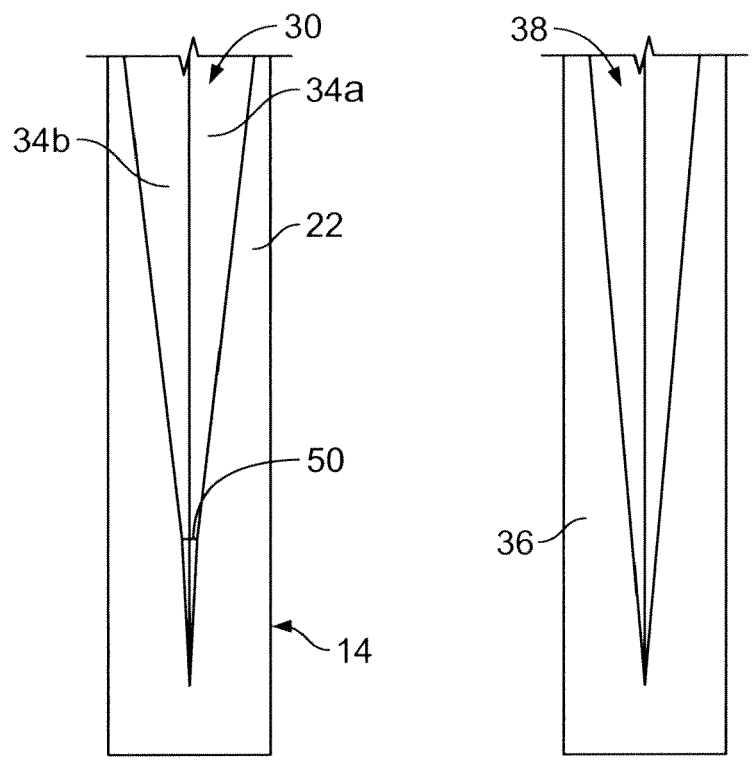
Amended FIG. 2    FIG. 3
                  PRIOR ART
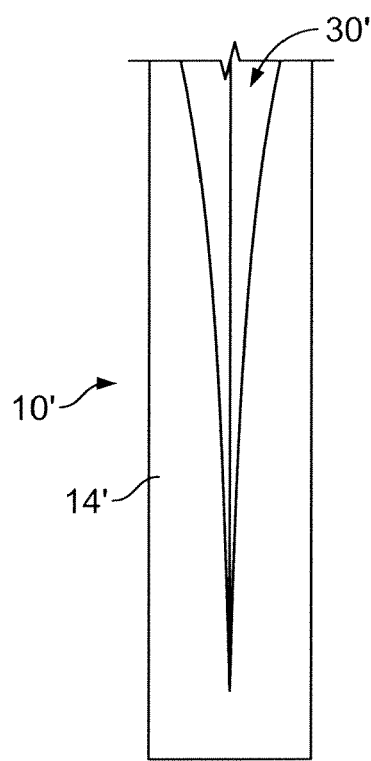
FIG. 6

PARALLEL-ACTING ROLLER CLAMP FOR INTRAVENOUS ADMINISTRATION SET

BACKGROUND OF THE INVENTION

This invention relates generally to parallel-acting roller clamps for regulating fluid flow through a deformable plastic tube in an intravenous (I.V.) administration set, and, more particularly, to parallel-acting roller clamps configured to provide improved control of fluid flow rate.

Parallel-acting roller clamps of this kind are commonly used as part of I.V. administration sets, for regulating the flow of a fluid being infused through a plastic infusion tube into a patient. The tube typically is formed of polyvinyl chloride (PVC) and is readily deformable. Such clamps typically include an elongated body having left and right side walls and a bottom wall, which cooperate to define an elongated chamber. A knurled roller wheel is located within the elongated chamber, with the ends of a wheel axle being supported within trunnion grooves formed in the left and right side walls. These grooves are arranged generally parallel with the bottom wall. The roller wheel, thereby, can be manually rolled along an axis substantially parallel with the bottom wall, while pinching the plastic infusion tube between the roller wheel and a clamping surface of the bottom wall. A relief groove is formed along the length of the bottom wall, having a transverse width that tapers from a maximum value at a first end to a minimum value at a second, opposite end. The relief groove typically is located along the centerline of the bottom wall, and the bottom wall's clamping surface is located on the left and right sides of such relief groove.

The body and roller wheel of the roller clamp are sized and configured such that the portions of the infusion tube sandwiched between the wheel and the clamping surface are pinched fully shut, while the portion of the infusion tube overlaying the relief groove is accommodated by the relief groove, to form a lumen for the flow of fluid. The size of the lumen, and thus the rate of fluid flow, is determined by the width of the relief groove immediately beneath the roller wheel.

Typically, the relief groove has a triangular cross-section defined by a pair of inclined walls, and the width of this relief groove tapers uniformly from its first end to its second end. Thus, the flow rate of fluid through the infusion tube can be made to vary from a maximum value, when the roller wheel is located at the relief groove's first end, to a minimum value, when the roller wheel is located at the relief groove's opposite, second end.

Parallel-acting roller clamps of this kind have functioned generally satisfactorily in regulating the flow of fluids being infused into patients. However, cold flow, or creep, of the portion of the plastic infusion tube being pinched by the roller wheel can, under certain circumstances, unduly affect the size of the formed lumen, and thus the stability of the fluid flow rate. Total flow rate variations in the range of 10 to 20 percent are generally considered acceptable; however, in some cases, unacceptably higher flow rate variations have been observed. Typically, about half of the total flow rate variation due to cold flow occurs within about 10 minutes after a flow rate adjustment has been made, with the remainder occurring over the next hour.

It should be appreciated from the foregoing description that there is a need for an improved parallel-acting roller clamp of a kind that minimizes variations in flow rate over time, due to cold flow or creep of its deformable plastic tube. The present invention satisfies this need and provides further related advantages.

SUMMARY OF THE INVENTION

The present invention is embodied in an improved parallel-acting roller clamp for regulating fluid flow through a deformable plastic tube, while minimizing time variations in flow rate due to cold flow or creep of the plastic tube. More particularly, the roller clamp includes an elongated body having left and right side walls and a bottom wall, such walls defining an elongated chamber, and it further includes a roller wheel located within the elongated chamber and configured to roll along an axis substantially parallel with the bottom wall, while pinching the plastic tube between the roller wheel and a clamping surface of the bottom wall. The bottom wall contains a relief groove extending along a substantial portion of the bottom wall's length, such relief groove having a transverse width that tapers monotonically from a maximum value at a first end to substantially zero at a second, opposite end. The portion of the relief groove located beneath the roller wheel accommodates a portion of the plastic tube located therebetween, with the transverse width of such relief groove portion determining the size of a lumen formed in the plastic tube and thereby regulating fluid flow through the tube. The convergence angle of the taper of the relief groove's transverse width is greater in a high-flow region, adjacent the relief groove's first end, than it is in a low-flow region, adjacent the relief groove's second end.

In other, more detailed features of the invention, the relief groove has a transverse cross-sectional shape that is triangular, defined by left and right inclined walls, and it is located along the bottom wall's longitudinal centerline. In one preferred configuration of the invention, the half convergence angle of the taper of the relief groove's transverse width has a first uniform value in the high-flow region and a second uniform value, lower than the first uniform value, in the low-flow region. Preferably, the first uniform value is in the range of 2.5 to 5.0 degrees, and the second uniform value is less than the first uniform value and less than 3.0 degrees. In addition, the relief groove's high-flow region, in one preferred configuration, extends along about three fourths of the relief groove's length, and its low-flow region extends along about one fourth of the relief groove's length. In an alternative preferred configuration of the invention, the relief groove has a tapered transverse width whose convergence angle varies continuously from a maximum value at first end to zero at its second end.

In yet other more detailed features of the invention, the relief groove extends over a majority of the bottom wall's length. Further, in one preferred configuration, the relief groove is located wholly within the clamping surface, e.g., along a centerline of the bottom wall, such that the clamping surface is located on both sides of the relief groove, between the relief groove and the left and right side walls. Further, the bottom wall and its relief groove are sized and configured such that the lumen formed in the portion of the plastic tube located beneath the roller wheel is located substantially only in the space within and above the relief groove.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIG. 1 is a perspective view of a parallel-acting roller clamp in accordance with a first embodiment of the present invention, for use in regulating fluid flow through a plastic infusion tube.

FIG. 2 is a top plan view of the bottom wall portion of the roller clamp of FIG. 1, showing a relief groove having a monotonically tapered transverse width that has a first uniform convergence half angle in a high-flow region and a second uniform convergence half angle, lower than the first uniform convergence half angle, in a low-flow region.

FIG. 3 is a top plan view, similar to FIG. 2, but of the bottom wall portion of a prior art roller clamp, including a relief groove having a tapered transverse width that has just a single convergence angle.

FIG. 6 is a top plan view of a second embodiment of a roller clamp in accordance with the invention, showing a relief groove having a monotonically tapered transverse width whose convergence angle decreases continuously from a high value in a high-flow region to zero in a low-flow region.

DESCRIPTION OF THE PREFERRED EMBODIMENTS

With reference now to the illustrative drawings, and particularly to FIGS. 1, 2, 4, and 5, there is shown a first embodiment of a parallel-acting roller clamp 10 in accordance with the invention, which is part of an intravenous (I.V.) administration set, for infusing a fluid through a plastic infusion tube 12 to a patient (not shown). The roller clamp is configured to allow a convenient and reliable regulation of the infusion fluid's flow rate.

Figure 4:
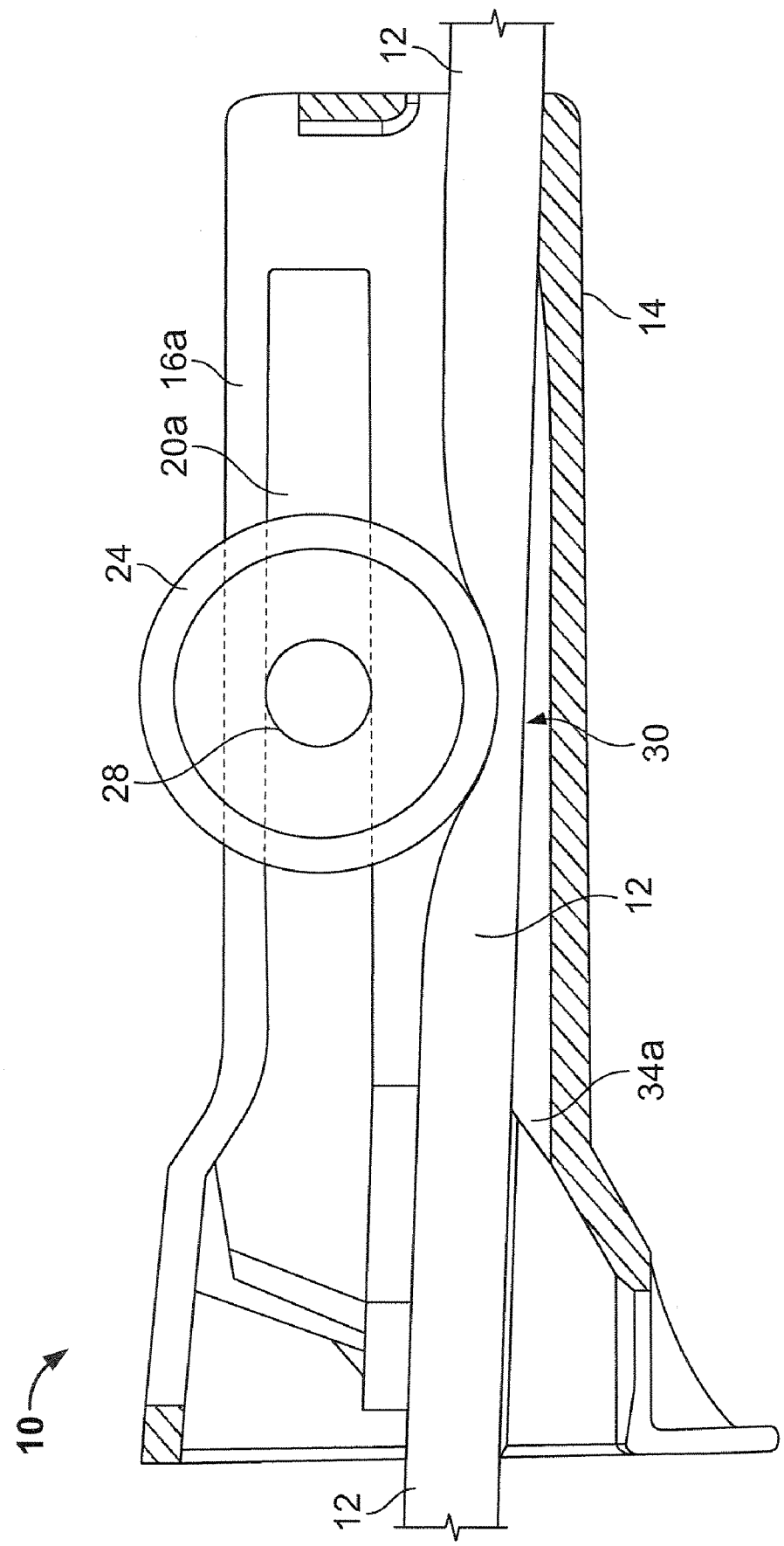
FIG. 4 is a cross-sectional view of the roller clamp, taken substantially in the direction of the arrows 4-4 in FIG. 1, showing the plastic infusion tube pinched between the roller wheel and the bottom wall.
Figure 5:
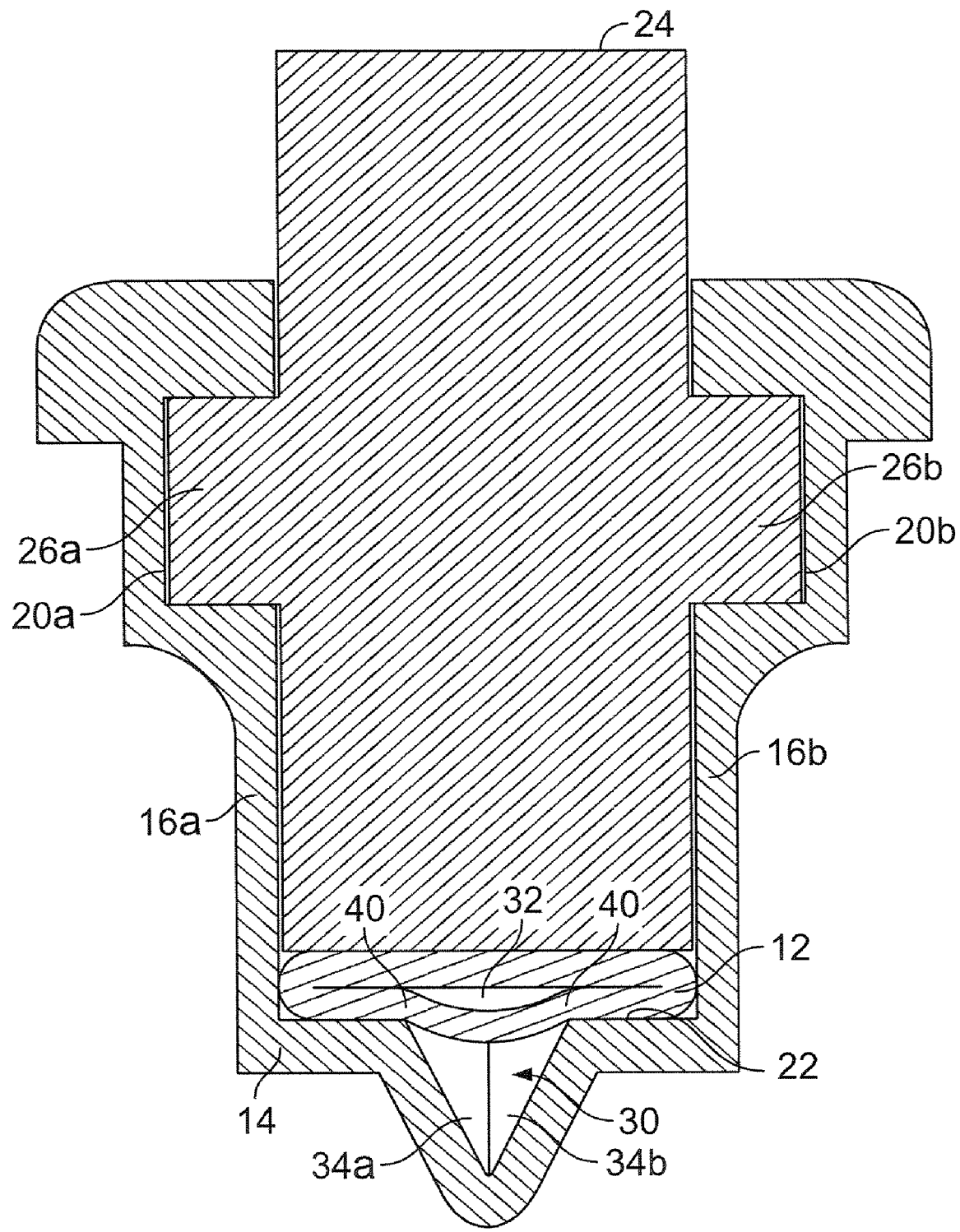
FIG. 5 is a cross-sectional view of the roller clamp, taken substantially in the direction of the arrows 5-5 in FIG. 1, showing the plastic infusion tube pinched between the roller wheel and the bottom wall.

The roller clamp 10 includes an elongated plastic body defined by a bottom wall 14, a left side wall 16a, and a right side wall 16b. The plastic body is integrally formed, e.g., by injection molding. As best shown in FIGS. 1 and 5, the left and right side walls project upward from the bottom wall's respective left and right side edges, to define an elongated chamber 18. The inward-facing sides of the left and right side walls are formed with trunnion grooves 20a, 20b extending along their length, parallel with the bottom wall's upper, or clamping surface 22. A knurled roller wheel 24 is located within the elongated chamber 18, with the left and right ends 26a, 26b of a wheel axle 28 being received in the respective left and right trunnion grooves 20a, 20b. The roller wheel, thereby, can be manually rolled from one end of the chamber to the other, while pinching the infusion tube 12 against the clamping surface 22.

The side walls 16a, 16b and the bottom wall 14 of the clamp body, and the knurled roller wheel 24, all are configured such that a narrow space is defined between the bottommost portion of the roller wheel and the bottom wall's clamping surface 22. The dimension of this space is less than twice that of the wall thickness of the undeformed plastic infusion tube 12.

A relief groove 30 is formed along the centerline of the bottom wall 14, extending over substantially the bottom wall's entire length. The relief groove's transverse width tapers monotonically from a maximum value adjacent one end to a minimum value adjacent the opposite end. The relief groove functions to accommodate a portion of the plastic infusion tube 12, with the portions of the bottom wall located on opposite sides of the relief groove forming the clamping surface 22, against which the tube is pinched by the roller wheel 24. A lumen 32 of restricted size is defined in the portion of the infusion tube located immediately beneath the roller wheel, within and above the relief groove 30.

The portions of the infusion tube 12 located on opposite sides of the relief groove 30, between the roller wheel 24 and the clamping surface 22, are pinched fully shut. The size of the lumen 32 is determined by the transverse width of the relief groove at the roller wheel's particular location, and this lumen size, in turn, determines the flow rate of the fluid being infused through the infusion tube. The flow rate is approximately proportional to the third power of the lumen's hydraulic radius.

When the knurled roller wheel 24 is positioned near the end of the elongated body adjacent the wide portion of the tapered relief groove 30, the roller clamp 10 provides a maximum flow rate. Conversely, when the roller wheel is positioned near the end of the elongated body adjacent the narrow portion of the tapered relief groove, the clamp provides a minimum flow rate, typically zero. Any selected flow rate between the maximum and minimum values can be provided by manually positioning the roller wheel at a particular position between the two ends.

The tapered relief groove 30 preferably has a triangular cross-section formed by a pair of divergent, or inclined, walls 34a, 34b. This configuration can be produced conveniently in the injection molding process in which the integral clamp body is formed.

In the past, the relief grooves of parallel-acting roller clamps of this kind typically have had a uniform convergence angle along their entire lengths. Such a configuration is depicted in FIG. 3, wherein the bottom wall is identified by the reference numeral 36 and the relief groove is identified by the reference numeral 38. Problems of unexpectedly large deviations in flow rate over time have been observed in the past, particularly in the clamp's low-flow region. Specifically, the flow rate has sometimes decreased substantially over time, reflecting a decrease in the size of the lumen formed beneath the roller wheel. About half of this decrease occurs during the first ten minutes after a flow rate adjustment has been made, and the remainder occurs over the next hour. Sometimes, this flow rate decrease has reached unacceptably high levels, requiring attendants to repeatedly monitor and adjust the roller wheel's position, to maintain the flow rate at the desired value.

It is believed that the fluid flow rate variations observed in prior roller clamps might have been caused by cold flow, or creep, in the portion of the plastic infusion tube being pinched by the roller wheel. The plastic tube typically is formed of polyvinyl chloride (PVC), which has a low elastic limit, and cold flow can occur when this elastic limit is exceeded. It further is believed that this cold flow phenomenon is particularly problematic when the roller wheel is positioned near the clamp's low-flow region, immediately adjacent to a flow cut-off point. It is in this region that the largest percentage changes in the flow rate provided by prior art roller clamps have been observed.

One solution to overcome the flow rate variation problem brought-on by cold flow, or creep, of the portion of the infusion tube located beneath the roller wheel is to modify the relief groove by decreasing the convergence angle of its transverse width. This positions the roller clamp's flow-cut-off point sufficiently away from the end of the relief groove in the low-flow region of concern that the effect of that end point is minimized. Such a modification, unfortunately, unduly increases the roller clamp's overall length.

Another solution, which is embodied in the roller clamp 10 of the invention, calls for the relief groove 30 to have a reduced taper angle only in the low-flow region, below a boundary line 50 (FIG. 2). The taper angle is increased over the remainder of the relief groove, including in particular the high-flow region. The taper in the high-flow region preferably has a convergence half angle in the range of 2.5 to 5.0 degrees, and the taper in the low-flow region preferably has a convergence half angle less than 3.0 degrees and less than that of the high-flow region. The high-flow region preferably extends along about three fourths of the relief groove's length, and the low-flow region preferably extends along the relief groove's remaining length.

With particular reference to FIG. 5, the cold flow phenomenon is believed to occur only in small transition sections 40 of the plastic tube 12 that are located within the relief groove 30 in a portion of the lumen wall and immediately adjacent to the portions of the tube being pinched between the roller wheel 24 and the clamping surface 22. Cold flow is believed to occur at a much reduced rate in other portions of the tube's cross-section, including the confined portions pinched between the roller wheel and the clamping surface, as well as the unconfined portions located in the major portion of the relief groove 30, spaced from the tube transition sections 40 and the relief groove's edges.

In the roller clamp's high-flow region, where the relief groove 30 has a relatively large width, the transition section of the plastic tube 12 exhibiting cold flow defines only a small fraction of the tube's lumen 32. In this high-flow region, the lumen is defined primarily by the tube's unconfined portion. Consequently, cold flow has only a small effect on flow rate in the clamp's high-flow region. In the clamp's low-flow region, on the other hand, where the relief groove 30 has a relatively small width, the transition section of the tube exhibiting cold flow represents a significant fraction of the tube's lumen. Consequently, cold flow can have a significant effect on flow rate in the clamp's low-flow region.

It has been found that the adverse effects of cold flow on the regulated fluid flow rate provided by the roller clamp 10 can be minimized if the end of the relief groove 30 is placed as far as possible from the roller wheel 24 for much of the clamp's low-flow region. Thus, as the roller wheel advances toward the shutoff position, the tube's left and right transition sections exhibiting cold flow converge toward each other and meet to create a shutoff at a position spaced from the end point. This is believed to minimize the adverse effects of cold flow.

With reference now to FIG. 6, there is shown a top plan view similar to the view of FIG. 2, but of a second embodiment of a roller clamp 10' in accordance with the invention. In this embodiment, the bottom wall 14' includes a relief groove 30' having a tapered transverse width whose convergence angle varies continuously from a maximum value at the clamp's high-flow region to a zero value at the clamp's low-flow region. Like the relief groove 30 of the first embodiment, this relief groove 30' extends along the bottom wall's centerline, over a substantial portion of the bottom wall's length.

It should be appreciated from the foregoing description that the present invention provides an improved parallel-acting roller clamp of a kind that regulates fluid flow through a plastic infusion tube with substantially reduced flow rate variation due to cold flow or creep of the tube, and with a more gradual adjustment of flow rate. The roller clamp achieves this improved performance by configuring the taper in the relief groove formed in the clamp's bottom wall to have a reduced convergence angle in the clamp's low-flow region or to have a convergence angle that decreases continuously from the high-flow region to the low-flow region.

It will be appreciated that the invention has been described in detail with reference only to the presently preferred embodiment. Those skilled in the art will appreciate that various modifications can be made without departing from the invention. Accordingly, the scope of the invention is defined only with reference to the following claims.

I claim:

1. A parallel-acting roller clamp for regulating fluid flow through a deformable plastic tube, comprising:
    an elongated body including left and right side walls and a bottom wall, such walls defining an elongated chamber;
    wherein the bottom wall defines a clamping surface having a length and a relief groove extending along a substantial portion of the clamping surface's length, such relief groove having
        a transverse width that defines a taper, and
        a pair of edges that converge monotonically from a maximum separation at a first end to a single point at a second, opposite end; and
    a roller wheel located at least partially within the elongated chamber and configured to roll along an axis substantially parallel with the clamping surface of the bottom wall, while directly contacting the plastic tube and pinching the plastic tube between the roller wheel and the clamping surface;
    wherein the portion of the relief groove located beneath the roller wheel accommodates a portion of the plastic tube located therebetween, with the transverse width of such relief groove portion determining the size of a lumen formed in the plastic tube and thereby regulating fluid flow through the tube;
    wherein the taper of the relief groove's transverse width defines a convergence angle that is greater in a high-flow region, adjacent the first end of the relief groove, than it is in a low-flow region, adjacent the second end of the relief groove; and
    wherein the transverse width of the relief groove narrows proximate the second end of the relief groove to create a shutoff position spaced from the second end.

2. A parallel-acting roller clamp as defined in claim 1, wherein the relief groove has a transverse cross-sectional shape that is triangular, defined by left and right inclined walls.

3. A parallel-acting roller clamp as defined in claim 1, wherein:
    the convergence angle of the taper of the relief groove's transverse width has a first uniform value in the high-flow region; and
    the convergence angle of the taper of the relief groove's transverse width has a second uniform value, lower than the first uniform value, in the low-flow region.

4. A parallel-acting roller clamp as defined in claim 3, wherein:
    the first uniform value has a half angle in the range of 2.5 to 5.0 degrees; and
    the second uniform value has a half angle less than that of the first uniform value and less than 3.0 degrees.

5. A parallel-acting roller clamp as defined in claim 4, wherein
    the high-flow region of the relief groove extends along about three fourths of the relief groove's length; and
    the low-flow region of the relief groove extends along about one fourth of the relief groove's length.

6. A parallel-acting roller clamp as defined in claim 1, wherein the convergence angle varies continuously from a maximum value at the first end of the relief groove to zero at the second end of the relief groove.

7. A parallel-acting roller clamp as defined in claim 1, wherein the relief groove extends over a majority of the clamping surface's length.

8. A parallel-acting roller clamp as defined in claim 1, wherein:
the relief groove extends along a centerline of the bottom wall; and
the clamping surface of the bottom wall is located on both sides of the relief groove, between the relief groove and the left and right side walls.

9. A parallel-acting roller clamp as defined in claim 1, wherein the bottom wall and its relief groove are sized and configured such that the lumen formed in the portion of the plastic tube located beneath the roller wheel is located substantially only in the space within and above the relief groove.

10. A parallel-acting roller clamp for regulating fluid flow through a deformable plastic tube, comprising:
an elongated body including left and right side walls and a bottom wall, such walls defining an elongated chamber;
wherein the bottom wall defines a clamping surface having a length and a relief groove extending longitudinally along a majority of the clamping surface's length and wholly within the clamping surface, such relief groove having a transverse cross-sectional shape that is triangular, defined by left and right inclined walls, and further having a transverse width that defines a taper, and further having a pair of edges that converge monotonically from a maximum separation at a first end to a single point at a second, opposite end; and
a roller wheel located at least partially within the elongated chamber and configured to roll along an axis substantially parallel with the clamping surface of the bottom wall, while directly contacting the plastic tube and pinching the plastic tube between the roller wheel and the clamping surface;
wherein the portion of the relief groove located beneath the roller wheel accommodates a portion of the plastic tube located therebetween, thereby defining a lumen located substantially only in the space within and above such relief groove portion, with the transverse width of such relief groove portion determining the size of the lumen and thereby regulating fluid flow through the tube;
wherein the roller clamp, adjacent the first end of the relief groove, includes a high-flow region, where the taper of the relief groove's transverse width defines a convergence angle having a first uniform half angle in the range of 2.5 to 5.0 degrees, and wherein the roller clamp, adjacent the second end of the relief groove, includes a low-flow region, where the taper of the relief groove's transverse width defines a convergence angle having a second uniform half angle less than the first uniform half angle and less than 3.0 degrees; and
wherein the transverse width of the relief groove narrows proximate the second end of the relief groove to create a shutoff position spaced from the second end.

11. A parallel-acting roller clamp as defined in claim 10, wherein the relief groove extends along a centerline of the bottom wall.

12. A parallel-acting roller clamp as defined in claim 10, wherein:
the high-flow region of the relief groove extends along about three fourths of the relief groove's length; and
the low-flow region of the relief groove extends along about one fourth of the relief groove's length.

* * * * *